United States Patent
Rabovsky et al.

(10) Patent No.: US 10,653,734 B2
(45) Date of Patent: *May 19, 2020

(54) DIETARY SUPPLEMENTS AND METHODS FOR TREATING PAIN AND INFLAMMATION

(71) Applicant: Melaleuca, Inc., Idaho Falls, ID (US)

(72) Inventors: Alexander B. Rabovsky, Idaho Falls, ID (US); Jeremy Ivie, Ammon, ID (US); Stephanie Nielson, Idaho Falls, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 661 days.

This patent is subject to a terminal disclaimer.

(21) Appl. No.: 15/164,418

(22) Filed: May 25, 2016

(65) Prior Publication Data

US 2017/0095519 A1    Apr. 6, 2017

Related U.S. Application Data

(63) Continuation of application No. 12/854,948, filed on Aug. 12, 2010, now Pat. No. 9,352,008.

(60) Provisional application No. 61/233,215, filed on Aug. 12, 2009.

(51) Int. Cl.
| | | |
|---|---|---|
| *A61K 36/185* | (2006.01) | |
| *A61K 36/73* | (2006.01) | |
| *A23L 33/105* | (2016.01) | |
| *A61K 36/232* | (2006.01) | |
| *A61K 36/82* | (2006.01) | |
| *A61K 36/9066* | (2006.01) | |
| *A61K 36/9068* | (2006.01) | |

(52) U.S. Cl.
CPC .......... *A61K 36/185* (2013.01); *A23L 33/105* (2016.08); *A61K 36/232* (2013.01); *A61K 36/73* (2013.01); *A61K 36/82* (2013.01); *A61K 36/9066* (2013.01); *A61K 36/9068* (2013.01); *A23V 2002/00* (2013.01)

(58) Field of Classification Search
CPC .... A61K 36/185; A61K 36/232; A61K 36/73; A61K 36/82; A61K 36/9066; A61K 2300/00; A61K 36/9068; A23V 2002/00; A23V 2200/30; A23V 2250/2112; A23V 2250/214; A23L 33/105; A23L 1/3002
USPC ......................................... 424/725, 729, 756
See application file for complete search history.

(56) References Cited

U.S. PATENT DOCUMENTS

| | | | |
|---|---|---|---|
| 3,615,721 A | 10/1971 | Silberman | |
| 3,758,682 A | 9/1973 | Huber et al. | |
| 4,393,085 A | 7/1983 | Spradlin et al. | |
| 4,698,360 A | 10/1987 | Masquelier | |
| 4,737,364 A | 4/1988 | Kalogris | |
| 5,009,891 A | 4/1991 | Niwa et al. | |
| 5,308,627 A | 5/1994 | Umbdenstock, Jr. | |
| 5,387,422 A | 2/1995 | Handel et al. | |
| 5,565,435 A | 10/1996 | Yoneyama et al. | |
| 5,567,424 A | 10/1996 | Hastings | |
| 5,569,458 A | 10/1996 | Greenberg | |
| 5,589,182 A | 12/1996 | Tashiro et al. | |
| 5,626,849 A | 5/1997 | Hastings et al. | |
| 5,904,924 A | 5/1999 | Gaynor et al. | |
| 5,948,443 A | 9/1999 | Riley et al. | |
| 5,976,568 A | 11/1999 | Riley | |
| 6,030,621 A | 2/2000 | De Long et al. | |
| 6,054,128 A | 4/2000 | Wakat | |
| 6,210,679 B1 | 4/2001 | Bailey et al. | |
| 6,224,871 B1 | 5/2001 | Hastings | |
| 6,280,737 B1 | 8/2001 | Stumpf et al. | |
| 6,344,220 B1 | 2/2002 | Rose et al. | |
| 6,358,526 B1 | 3/2002 | Mergens et al. | |
| 6,413,554 B1* | 7/2002 | No ....................... | A61K 36/232 424/725 |
| 6,713,096 B2 | 3/2004 | Cho | |
| 7,138,149 B2 | 11/2006 | Cho | |
| 9,352,008 B2 | 5/2016 | Rabovsky et al. | |
| 2003/0194435 A1 | 10/2003 | Mercati | |
| 2007/0154575 A1 | 7/2007 | Shimoda et al. | |
| 2009/0252796 A1 | 10/2009 | Mazed et al. | |
| 2010/0021533 A1 | 1/2010 | Mazed et al. | |
| 2010/0178288 A1* | 7/2010 | Gokaraju ............... | A61K 36/58 424/94.65 |

FOREIGN PATENT DOCUMENTS

| | | |
|---|---|---|
| KR | 10-1998-0025262 | 7/1998 |
| KR | 10-2002-0024127 | 3/2002 |
| KR | 10-0415826 | 1/2004 |
| KR | 10-2004-0079393 | 9/2004 |
| KR | 10-0858768 | 9/2008 |

(Continued)

OTHER PUBLICATIONS

Authorized officer K. Kim. International Preliminary Report on Patentability in International Application No. PCT/US2010/045260, dated Feb. 23, 2012, 7 pages.

(Continued)

*Primary Examiner* — Aaron J Kosar

(74) *Attorney, Agent, or Firm* — Fish & Richardson P.C.

(57) ABSTRACT

The document provides compositions such as dietary supplements. Such compositions can be used to reduce pain, inflammation, stiffness, and/or discomfort associated with inflammatory conditions such as arthritis. The document also provides methods for reducing pain, inflammation, stiffness, and/or discomfort associated with inflammatory conditions such as arthritis.

20 Claims, 3 Drawing Sheets

(56) References Cited

FOREIGN PATENT DOCUMENTS

| WO | WO 2001/015553 | 3/2001 |
|---|---|---|
| WO | WO 2001/052841 | 7/2001 |
| WO | WO 2006/093793 | 9/2006 |

OTHER PUBLICATIONS

Authorized officer K. Kim. International Search Report and Written Opinion in International Application No. PCT/US2010/045260, dated Apr. 21, 2011, 10 pages.
Search Report for Taiwanese Application No. 099126888 completed Mar. 18, 2015, 2 pages.
"Plant derivatives for pharmaceuticals," Indena [online], [retrieved on Aug. 13, 2002], Retrieved from the Internet: < URL: http://www.indena.it/pharmac.htm>, 4 pages.
"Ultimate Joint Repair Formula," The Health Store [online] [retrieved on Mar. 24, 2003] Retrieved from the Internet: < URL: http://www.thehealthstore.net/en-us/p_2.html>, 1 page.
Altman and Marcussen, "Effects of a ginger extract on knee pain in patients with osteoarthritis," *Arthritis Rheum.*, 2001, 44:2531-2538.
American Biologics, "Ultra Inflazyme Forte™" Jan. 2002, 2 pages.
Bachmeier et al., "Curcumin downregulates the inflammatory cytokines CXCL1 and -2 in breast cancer cells via NFkB," *Carcinogenesis*, 2008, 29(4) 779-789, Advance Access publication Nov. 13, 2007.
Balch and Balch, *Prescription for Nutritional Healing*, Second Edition, 1997, pp. 20-21 and 47-48.
Bliddal et al., "A randomized, placebo-controlled, cross-over study of ginger extracts and ibuprofen in osteoarthritis," *Osteoarthritis Cartilage*, 2000, 8:9-12.
Bombardelli, "Phytosome®: new cosmetic delivery system," *Boll. Chim. Farmaceutico*, 1991, 8 pgs.
Broncelet al., [Effect of anthocyanins from Aronia melanocarpa on blood pressure, concentration of endothelin-1 and lipids in patients with metabolic syndrome], *Pol. Merkur Lekarski.*, 2007, 23:116-119.
Cao et al., "Increases in human plasma antioxidant capacity after consumption of controlled diets high in fruit and vegetables," *Am. J. Clin. Nutr.*, 1998, 68:1081-1087.
Choi et al., "Antinociceptive mechanisms of orally administered decursinol in the mouse," *Life Sci.*, 2003, 73:471-485.
Choi et al., "Antinociceptive profiles of crude extract from roots of Angelica gigas NAKAL in various pain models," *Biol. Pharm. Bull.* 2003. 26:1283-1288.
Chrubasik et al., "Comparison of outcome measures during treatment with the proprietary Harpagophytum extract doloteffin in patients with pain in the lower back, knee or hip," *Phytomedicine*, 2002, 9:181-194.
Chrubasik et al., "Physicochemical properties of harpagoside and its in vitro release from Harpagophytum procumbens extract tablets," *Phytomedicine*. 2000, 6:469-473.
Dallas et al., "Degradation of oligomeric procyanidins and anthocyanins in Tinta Roriz red wine during maturation," *Vitis*, 1995, 34(1):51-56.
Demrow et al., "Administration of Wine and Grape Juice Inhibits In Vivo Platelet Activity and Thrombosis in Stenosed Canine Coronary Arteries," *Circulation*, 1995, 91(4):1182-1188.
Eichhorn et al., "Spontaneous Alterations in Coronary Blood Flow Velocity Before and After Coronary Angioplasty in Patients With Severe Angina," *JACC*, 1991, 17(1):43-52.
Folts and Osman, "Platelet Inhibitory Effect of Feeding Grape Juice But Not Orange or Grapefruit Juice for Seven Days in Monkeys," *Supplement to JACC*, 1997, 29(2, Suppl. A):303A, Abstract No. 1006-156, 3 pages.
Folts et al., "Grape Juice But Not Orange or Grapefruit Juice Significantly Inhibits In Vivo Platelet Activity and Thrombosis in Stenosed Canine Coronary Arteries," *Supplement to JACC*, 1997, 29(2, Suppl. A):180A, Abstract No. 734-5, 2 pages.
Folts et al., "Moderate alcohol consumption, CAD, and myocardial ischemia," *J. Myocardial Ischemia*, 1994, 6(8):33-40.

Folts et al., "Platelet Aggregation in Partially Obstructed Vessels and its Elimination with Aspirin," *Circulation*, 1976, 54:365-370.
Folts et al., "Possible Platelet Thrombi Formation in Dog and Human Femoral Arteries," *Texas Heart Institute Journal*, 1982, 9(1):19-26.
Folts, "An In Vivo Model of Experimental Arterial Stenosis, Intimal Damage, and Periodic Thrombosis," *Supplement to Circulation*, 1991, 83(Suppl. IV):IV-3-IV-14.
Folts, "Drugs for the prevention of coronary thrombosis: from an animal model to clinical trials," *Cardiovasc Drugs Ther.*, 9(1):31-43, Jan. 1, 1995.
Folts, "Flavonoid in Tea but not Coffee Given by Gastric Tube Inhibit In Vivo Platelet Activity and Thrombus Formation in Stenosed Dog Coronary Arteries," *FASEB J.*, p. A793, Abstract No. 4579, 2 pages, 1996.
Folts, "Gastric Administration of a Commercial Flavonoid Dietary Supplement Inhibits In Vivo Platelet Activity and Cyclic Flow Reductions in Stenosed Monkey Carotid Arteries," *Supplement to Circulation*, Abstracts from the $68^{th}$ Scientific Sessions, Anaheim, California, p. I-489, Abstract No. 2336, 1995, 2 pages.
Folts, "Three Glasses of Grape But Not Orange or Grapefruit Juice Inhibit Ex Vivo Platelet Aggregation in Human Volunteers," *Supplement to JACC*, 1997, 29(2, Suppl. A):226A, Abstract No. 767-3, 2 pages.
Formica and Regelson, "Review of the Biology of Quercetin and Related Bioflavonoids," *Food Chem. Toxic.*, 1995, 33(12):1061-1080.
Funk, J et al. "Turmeric extracts containing curcuminoids prevent experimental rheumatoid arthritis," *J Nat Prod.*, 69(3):351-355, Mar. 2006.
Haqqi et al., "Prevention of collagen-induced arthritis in mice by a polyphenolic fraction from green tea." *Proc. Natl. Acad. Sci. USA*, 96: 4524-4529, 1999.
Hashimoto et al., "Effect of Acute Intake of Red Wine on Flow-Mediated Vasodilatation of the Brachial Artery," *Am. J. Cardiol.*, 2001, 88:1457-1460.
Jang et al., "*Harpagophytum procumbens* suppresses lipopolysaccharide-stimulated expressions of cyclooxygenase-2 and inducible nitric oxide synthase in fibroblast cell line L929," *J Pharmacol. Sci.*, 2003, 93:367-371.
Kim et al., "Curcumin attenuates inflammatory responses of TNF-alpha-stimulated human endothelial cells," *J Cardiovasc. Pharmacol.*, 2007, 50:41-49.
Kumar, V. et al., "Biodegradable microspheres of curcumin for treatment of inflammation," Indian J Physiol Pharmacol. Apr. 2002; 46(2): 209-217, Abstract.
Leblan et al., "Harpagophytum procumbens in the treatment of knee and hip osteoarthritis. Four-month results of a prospective, multicenter, double-blind trial versus diacerhein," *Joint Bone Spine*, 2000, 67:462-467.
Levy, Asa et al. BMC Pharmacology (2006); 6-Shogaol reduced chronic inflammatory response in the knees of rats treated with complete Freund's adjuvant. (6): 1-8.
Marcus et al., "Is there a role for ginger in the treatment of osteoarthritis?" *Arthritis Rheum.*, 2001, 44:2461-2462.
Marlyn Nutraceuticals, Inc., "Wobenzym-N," Vitamin Express [online] copyright 1996-2003 [retrieved on Mar. 27, 2003] Retrieved from the Internet:< URL: http://www.vitaminexpress.com/prodinfo/wobenzym_n.htm>, 2 pages.
Morris et al., "Effects of Fruit Maturity, Juice Storage, and Juice Extraction Temperature on Quality of 'Concord' Grape Juice," *J. Amer. Soc. Hort. Sci.*, 1986, 111(5):742-746.
Ohgami et al., "Anti-inflammatory effects of aronia extract on rat endotoxin-induced uveitis," *Invest Ophthalmol. Vis. Sci.*, 2005, 46:275-281.
Preuss et al., "Effects of Niacin-Bound Chromium and Grape Seed Proanthocyanidin Extract on the Lipid Profile of Hypercholesterolemic Subjects: A Pilot Study," *J. Med.*, 2000, 31(5 & 6):227-246.
PTOL-413B (04-03): Examiner-Initiated Interview Summary dated Apr. 17, 2006 with attached "Dr. Stan Guberman Invoice.".
RX Vitamins™, "NutriFlex for Dogs and Cats," RX Vitamins [online] [retrieved on Mar. 24, 2003]Retrieved from the Internet: < URL: http://www.rxvitamins.com/pets/nutriflex.asp>, 2 pages.

(56) References Cited

OTHER PUBLICATIONS

Saja et al., "Anti-inflammatory effect of curcumin involves downregulation of MMP-9 in blood mononuclear cells," *Int. Immunopharmacol.*, 2007, 7:1659-1667.

Shakibaei et al., "Suppression of NF-kappaB activation by curcumin leads to inhibition of expression of cyclo-oxygenase-2 and matrix metalloproteinase-9 in human articular chondrocytes: Implications for the treatment of osteoarthritis," *Biochem. Pharmacol.*, 2007, 73:1434-1445.

Sharma et al., "Suppressive effects of eugenol and ginger oil on arthritic rats," *Pharmacology*, 49(5):314-318, 1994.

Singleton and Rossi, Jr., "Colorimetry of Total Phenolics with Phosphomolybdic-Phosphotungstic Acid Reagents," *Am. J. Enol. Vitic*, 1965, 16:144-158.

Slane et al., "Platelet Inhibition in Stenosed Canine Arteries by Quercetin and Rutin, Polyphenolic Flavonoids Found in Red Wine," *Clinical Research*, 1994, 42(2):162A, Abstract, 2 pages.

Strong et al., "Prevalence and Extent of Atherosclerosis in Adolescents and Young Adults," *JAMA*, 1999, 281(8):727-735.

Strong, "Atherosclerosis in the Young: Risk and Prevention," *Hospital Practice*, 1999, pp. 15, 16 and 19.

Suekawa et al., [Pharmacological studies on ginger. IV. Effect of (6)-shogaol on the arachidonic cascade], *Nippon Yakurigaku Zasshi*, 1986, 88:263-269.

Takahashi et al., "Suppression of adjuvant arthritis by oral administration of oriental herbs II," *Kitasato Arch. Exp. Med.*, 1982, 55:39-45.

Tjendraputra, et al., "Effect of ginger constituents and synthetic analogues on cyclooxygenase-2 enzyme in intact cells," *Bioorg. Chem.*, 2001, 29:156-163.

Uni Key Health Systems, Inc., "Infla-Zyme Forte," UniKey [online] 2001 [retrieved on Mar. 27, 2003]. Retrieved from the Internet: <URL: http://www.unikeyhealth.com/products_cleansing_inflazyme.asp>, 2 pages.

Valcheva-Kuzmanova et al., "Hypoglycemic and hypolipidemic effects of Aronia melanocarpa fruit juice in streptozotocin-induced diabetic rats," *Methods Find. Exp. Clin. Pharmacol.*, 2007, 29:101-105.

Waterhouse et al., "The Phenolic Phytochemicals in Wine, Fruit and Tea: Dietary Levels, Absorption and Potential Nutritional Effects," *Hypernutritious Foods*, 1996, Finley et al. (eds.), Agscience, Inc., Chapter 14, pp. 219-238.

Wegener et al., "Treatment of patients with arthrosis of hip or knee with an aqueous extract of devil's claw (*Harpagophytum procumbens* DC.)," *Phytother. Res.*, 2003, 17:1165-1172.

Wobenzyme N (Enzyme) 800 TB, Healing Edge Sciences [online] [retrieved on Mar. 27, 2003]. Retrieved from the Internet: < URL: http://www.healingedge.net/store/more_mar_wobenzyme.html>, 4 pages.

Wood et al., "Sequential effects of an oral enzyme combination with rutosid in different in vitro and in vivo models of inflammation," *Int. J. Immunotherapy*, XIII (3/4): 139-145, 1997.

\* cited by examiner

DIETARY SUPPLEMENTS AND METHODS FOR TREATING PAIN AND INFLAMMATION

CROSS-REFERENCE TO RELATED APPLICATIONS

This application is a Continuation of U.S. application Ser. No. 12/854,948, filed Aug. 12, 2010 (now U.S. Pat. No. 9,352,008), which claims priority under 35 U.S.C. § 119(e) to U.S. Application Ser. No. 61/233,215, filed on Aug. 12, 2009, which are incorporated by reference in their entirety herein.

BACKGROUND

1. Technical Field

This document relates to dietary supplements as well as methods and materials for reducing pain, inflammation, and stiffness associated with inflammatory conditions such as arthritis.

2. Background Information

Inflammatory conditions such as arthritis and osteoarthritis are serious medical problems that affect many Americans. In fact, arthritis is one of the nation's most prevalent chronic health problems. An estimated 43 million Americans suffer from some form of arthritis. According to the Arthritis Foundation, this figure is expected to jump to about 60 million within the next decade.

Osteoarthritis (OA), also known as degenerative joint disease, is the most common form of arthritis. By age 40, about 90 percent of all people have x-ray evidence of OA in the weight bearing joints such as the hips and knees. In addition, more than 20 million Americans currently have symptoms of OA. Severe involvement of the hips, knees, and spinal column can greatly limit activity and diminish the overall quality of life. The gradual breakdown of cartilage that accompanies aging is the leading cause of OA. This type of OA, called primary osteoarthritis, is caused by cartilage damage resulting mostly from stress on the joint from, for example, obesity. The first alteration in the joint, which takes place over decades, is a roughening of articular cartilage followed by pitting, ulceration, and progressive loss of cartilage surface. Primary OA most commonly involves the joints of the fingers, hips, knees, spine, base of the thumb, and big toe. It can be present in just one of these joints or in all of them.

Secondary OA, however, can affect any joint. Typically, secondary OA follows trauma or chronic joint injury due to some other type of arthritis such as rheumatoid arthritis. Alternatively, secondary OA can result from overuse of a particular joint. Although most body tissues can make repairs following an injury, cartilage repair is hampered by a limited blood supply and the lack of an effective mechanism for cartilage re-growth. The effects of joint overuse were shown in a study that revealed that subjects whose jobs required at least one hour a day of kneeling or squatting were almost twice as likely to have OA in the knees than those not commonly performing such activities. Because trauma or overuse hastens the degeneration of cartilage, symptoms of secondary OA can become apparent at a much younger age than symptoms of primary OA.

There are number of treatments that can relieve the pain, inflammation, and discomfort associated with OA. One treatment involves the use of non-steroidal anti-inflammatory drugs (NSAIDs). Although NSAIDs relieve some stiffness, inflammation, and pain associated with OA, NSAIDs can lead to side effects such as gastric bleeding, liver damage, and kidney damage. In addition, long-term use of NSAIDs can lead to reduced effectiveness.

SUMMARY

This document provides methods and materials related to reducing pain, inflammation, and/or stiffness associated with inflammatory conditions such as arthritis and OA. For example, the document provides compositions (e.g., dietary supplements) containing an iridoid, a ginger component, an anthocyanin, a coumarin, a curcuminoid, and a green tea extract. In some cases, a composition provided herein can contain a Devil's Claw extract, a ginger component, an *Aronia* extract, an *Angelica gigas* extract, a turmeric extract, and/or a green tea extract.

Non-limiting examples of an iridoid can include harpagoside, loganin, sweroside, vogeloside, and epi-vogeloside. In some cases, the iridoid can be harpagoside. In certain cases, the iridoid can be a component of a plant extract. For example, the iridoid can be a component in a Devil's claw extract.

In some cases, the ginger component can be a ginger root extract.

An anthocyanin can be, for example, one or more of aurantinidin, cyaniding, delphinidin, europinidin, luteolinidin, pelargonidin, malvidin, peonidin, petunidin, rosinidin. In some cases, the anthocyanin can be a component of a plant extract. For example, the anthocyanin can be a component of an *Aronia* extract (e.g., *Aronia melanocarpa*).

Non-limiting examples of a coumarin include decursin, decursinol, nodakenetin, umbelliferon, nodakenin, and β-sitosterol. In some cases, the coumarin can be decursinol. In some cases, the coumarin can be a component of a plant extract. For example, the coumarin can be a component of an *Angelica gigas* extract (e.g., an *Angelica gigas* root extract).

In some cases, a curcuminoid can be curcumin. In certain cases, the curcuminoid is a component of a plant extract. For example, the curcuminoid can be a component of a turmeric extract.

A green tea extract can include, for example, one or more of a catechin, epicatechin, gallocatechin, epigallocatechin, epicatechin gallate, epicatchingallate, and epigallocatechin gallate. In some cases, the green tea extract comprises epigallocatechin gallate.

In some cases, the composition (e.g., dietary supplement) includes:
  (a) about 150 to about 250 mg/serving of a Devil's Claw extract;
  (b) about 135 to about 225 mg/serving of a ginger component;
  (c) about 65 to about 115 mg/serving of an *Aronia* extract;
  (d) about 35 to about 65 mg/serving of an *Angelica gigas* extract;
  (e) about 15 to about 35 mg/serving of a turmeric extract; and
  (f) about 45 to about 75 mg/serving of a green tea extract.
For example, the composition can include:
  (a) about 200 mg/serving of a Devil's Claw extract;
  (b) about 180 mg/serving of a ginger component;
  (c) about 90 mg/serving of an *Aronia* extract;
  (d) about 50 mg/serving of an *Angelica gigas* extract;
  (e) about 25 mg/serving of a turmeric extract; and
  (f) about 60 mg/serving of a green tea extract.

In some cases, the composition can be in the form of a tablet, powder or a liquid. For example, a tablet can include:

(a) about 150 to about 250 mg/serving of a Devil's Claw extract;
(b) about 135 to about 225 mg/serving of a ginger component;
(c) about 65 to about 115 mg/serving of an *Aronia* extract;
(d) about 35 to about 65 mg/serving of an *Angelica gigas* extract;
(e) about 15 to about 35 mg/serving of a turmeric extract; and
(f) about 45 to about 75 mg/serving of a green tea extract.

In other cases, a dietary supplement can include:

(a) about 37 to about 63 mg/serving of a Devil's Claw extract;
(b) about 33 to about 57 mg/serving of a ginger component;
(c) about 16 to about 29 mg/serving of an *Aronia* extract;
(d) about 8 to about 16 mg/serving of an *Angelica gigas* extract;
(e) about 3 to about 8 mg/serving of a turmeric extract; and
(f) about 11 to about 19 mg/serving of a green tea extract.

For example, a dietary supplement can include:

(a) about 50 mg/serving of a Devil's Claw extract;
(b) about 45 mg/serving of a ginger component;
(c) about 22.5 mg/serving of an *Aronia* extract;
(d) about 12.5 mg/serving of an *Angelica gigas* extract;
(e) about 6.25 mg/serving of a turmeric extract; and
(f) about 15 mg/serving of a green tea extract.

Also provided herein is a method of reducing pain, stiffness, or inflammation in a mammal. The method can include administering to the mammal a dietary supplement having an iridoid, a ginger component, an anthocyanin, a coumarin, a curcuminoid, and a green tea extract. In some cases, daily administration of the dietary supplement to the mammal for at least one week reduces pain, stiffness, or inflammation in the mammal.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
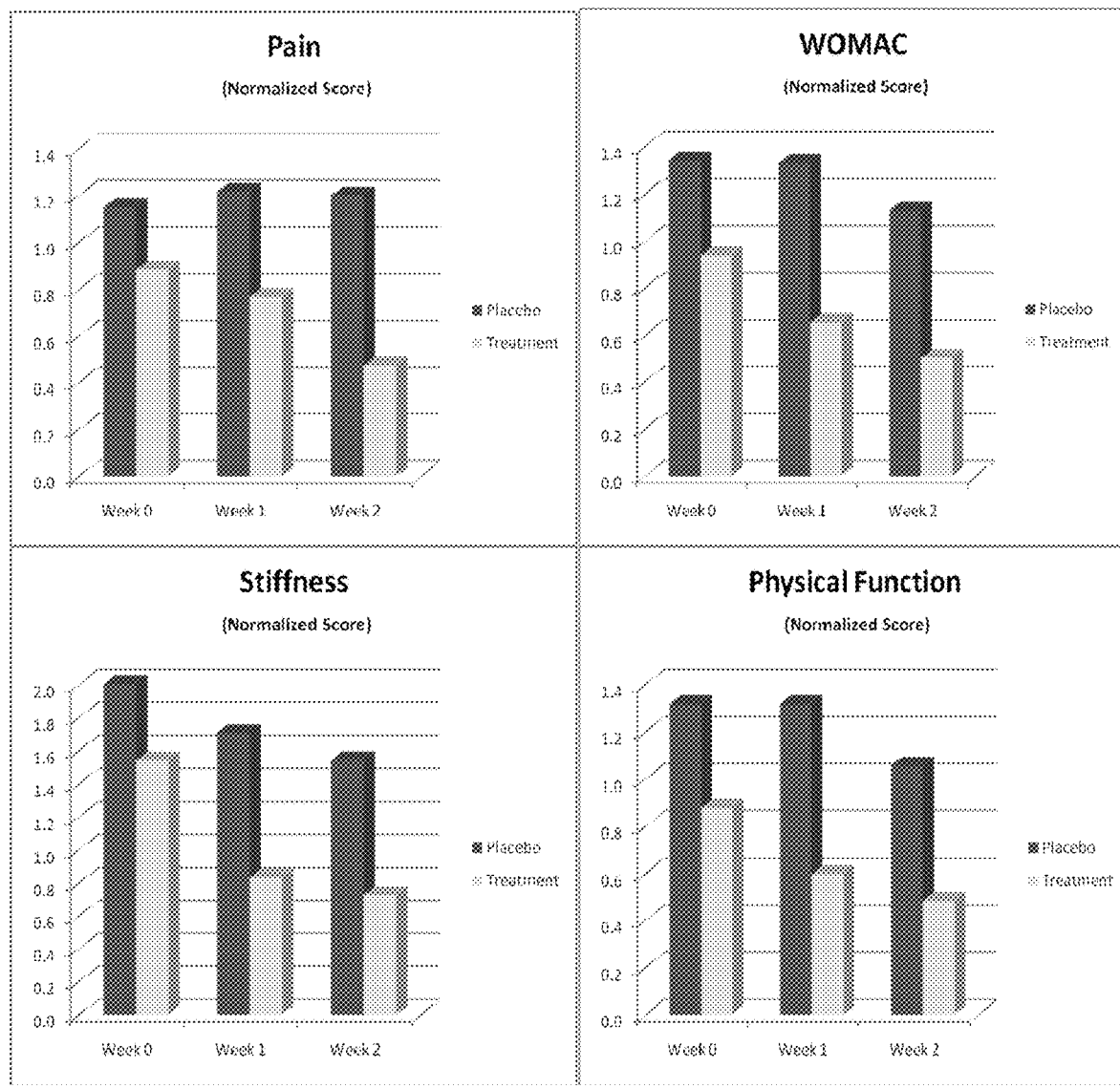
FIG. 1 is a bar graph of the averaged normalized WOMAC scores for each category tested.

This document provides methods and materials related to reducing pain, inflammation, and/or stiffness associated with inflammatory conditions such as arthritis and OA. For example, the document provides compositions (e.g., dietary supplements) containing an iridoid, a ginger component, an anthocyanin, a coumarin, a curcuminoid, and a green tea extract. In some cases, a composition provided herein can contain a Devil's Claw extract, a ginger component, an *Aronia* extract, an *Angelica gigas* extract, a turmeric extract, and/or a green tea extract.

Iridoid

A composition described herein can contain an iridoid. Examples of iridoids include, without limitation, harpagoside, loganin, sweroside, vogeloside, and epi-vogeloside. In some cases, the iridoid is harpagoside:

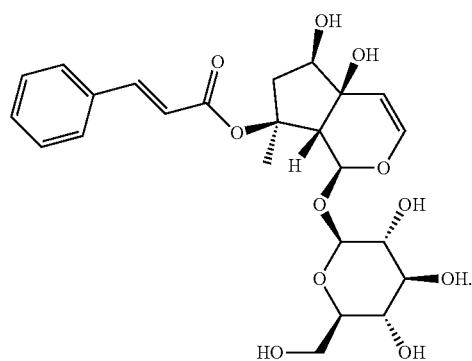 [SMILES: C[C@]1(OC(=O)/C=C/c2ccccc2)C[C@@H](O)[C@]2(O)C=CO[C@@H](O[C@@H]3O[C@H](CO)[C@@H](O)[C@H](O)[C@H]3O)[C@@H]21]

Iridoids can be synthesized or derivatized from natural sources. In some cases, an iridoid can be a component of a plant extract. For example, an iridoid can be a component of an extract of Devil's Claw. A Devil's Claw extract can be made using an ethanol or hydroalcoholic extraction. In some cases, iridoids and/or plant extracts containing iridoids (e.g., Devil's Claw) can be obtained commercially. For example, Devil's Claw extract can be obtained from Pharmline Inc., (NY, USA).

A composition described herein can contain one or more than one iridoid. In some cases, a composition can contain any amount of an iridoid. For example, at least 5 percent (e.g., at least 10, 15, 20, 25, 30, 35, 40, 50, 60, 70, 80, or 90 percent) of a dietary supplement can be an iridoid. Typically, a dietary supplement contains between 5 mg and 5000 mg (e.g., between 5 mg and 4500 mg, between 5 mg and 4000 mg, between 5 mg and 3500 mg, between 5 mg and 3200 mg, between 5 mg and 3000 mg, between 5 mg and 2500 mg, between 5 mg and 1500 mg, between 5 mg and 1000 mg, between 5 mg and 750 mg, between 5 mg and 600 mg, between 5 mg and 500 mg, between 5 mg and 400 mg, between 5 mg and 300 mg, between 5 mg and 250 mg, between 5 mg and 100 mg, between 5 mg and 50 mg, between 25 mg and 5000 mg, between 50 mg and 5000 mg, between 100 mg and 5000 mg, between 250 mg and 5000 mg, between 350 mg and 5000 mg, between 500 mg and 5000 mg, between 625 mg and 5000 mg, between 700 mg and 5000 mg, between 900 mg and 5000 mg, between 1000 mg and 5000 mg, between 1500 mg and 5000 mg, between 2000 mg and 5000 mg, between 3500 mg and 5000 mg, between 5 mg and 1000 mg, between 25 mg and 500 mg, between 50 mg and 400 mg, between 100 mg and 300 mg, and between 150 mg and 250 mg) of an iridoid. A composition can be formulated to contain an amount of an such that a daily dose of between 300 mg and 3000 mg (e.g., between 300 and 2500 mg, between 300 mg and 2000 mg, between 300 mg and 1500 mg, between 300 mg and 1250 mg, between 300 mg and 900 mg, between 400 mg and 3000 mg, between 500 mg and 3000 mg, between 650 mg and 3000 mg, between 700 mg and 3000 mg, between 775 mg and 3000 mg, between 400 mg and 2000 mg, between 500 mg and 1500 mg, between 600 mg and 1200 mg, between 700 mg and 800 mg) of the iridoid can be conveniently administered.

In some cases, the iridoid can be a component of a plant extract. For example, the iridoid can be a component of a Devil's Claw extract. In some cases, the Devil's Claw extract is obtained using standard extraction techniques. In some cases, a composition can contain any amount of a plant extract, such as a standard Devil's claw extract. For example, at least 5 percent (e.g., at least 10, 15, 20, 25, 30, 35, 40, 50, 60, 70, 80, or 90 percent) of a dietary supplement can be the plant extract. Typically, a dietary supplement contains between 50 mg and 5000 mg (e.g., between 5 mg and 4500 mg, between 5 mg and 4000 mg, between 5 mg and 3500 mg, between 5 mg and 3200 mg, between 5 mg and 3000 mg, between 5 mg and 2500 mg, between 5 mg and 1500 mg, between 5 mg and 1000 mg, between 5 mg and 750 mg, between 5 mg and 600 mg, between 5 mg and 500 mg, between 5 mg and 400 mg, between 5 mg and 300 mg, between 5 mg and 250 mg, between 5 mg and 100 mg, between 5 mg and 50 mg, between 25 mg and 5000 mg, between 50 mg and 5000 mg, between 100 mg and 5000 mg, between 250 mg and 5000 mg, between 350 mg and 5000 mg, between 500 mg and 5000 mg, between 625 mg and 5000 mg, between 700 mg and 5000 mg, between 900 mg and 5000 mg, between 1000 mg and 5000 mg, between 1500 mg and 5000 mg, between 2000 mg and 5000 mg, between 3500 mg and 5000 mg, between 5 mg and 1000 mg, between 25 mg and 500 mg, between 50 mg and 400 mg, between 100 mg and 300 mg, and between 150 mg and 250 mg) of the plant extract. A composition can be formulated to contain an amount of the plant extract such that a daily dose of between 300 mg and 3000 mg (e.g., between 300 and 2500 mg, between 300 mg and 2000 mg, between 300 mg and 1500 mg, between 300 mg and 1250 mg, between 300 mg and 900 mg, between 400 mg and 3000 mg, between 500 mg and 3000 mg, between 650 mg and 3000 mg, between 700 mg and 3000 mg, between 775 mg and 3000 mg, between 400 mg and 2000 mg, between 500 mg and 1500 mg, between 600 mg and 1200 mg, between 700 mg and 800 mg) of the plant extract can be conveniently administered.

Ginger

A composition described herein can contain a ginger component. Examples of ginger components include, without limitation, dried ginger (e.g., dried gingerroot), ginger oil, and ginger extracts. In some cases, a ginger component can be a ginger root extract. A ginger component can be obtained from any of the estimated 1300 species of plants that belong to the Zingiberaceae family. Typically, a ginger component is derived from *Zingiber officinale, Alpinia officnarum*, or *Alpinia galanga*.

Any method can be used to prepare a ginger component. For example, standard harvesting and drying methods can be used to prepare dried gingerroot. Ginger oil can be obtained using standard methods and processed with cellulose for making tablet or powder compositions. A ginger extract can be made using an ethanol or hydroalcoholic extraction. Such extracts can be standardized to, for example, 5 to 75 percent gingerol or shogaol. In some cases, ginger components can be obtained commercially. For example, dried ginger, ginger oil, and ginger extract can be obtained from BattleChem Inc., (CA, USA). A composition of the invention can contain one or more than one ginger component. For example, a dietary supplement can contain dried gingerroot as well as a ginger root extract. In some cases, a composition can contain any amount of a ginger component. For example, at least 5 percent (e.g., at least 10, 15, 20, 25, 30, 35, 40, 50, 60, 70, 80, or 90 percent) of a dietary supplement can be a ginger component. Typically, a dietary supplement contains between 5 mg and 5000 mg (e.g., between 5 mg and 4500 mg, between 5 mg and 4000 mg, between 5 mg and 3500 mg, between 5 mg and 3200 mg, between 5 mg and 3000 mg, between 5 mg and 2500 mg, between 5 mg and 1500 mg, between 5 mg and 1000 mg, between 5 mg and 750 mg, between 5 mg and 600 mg, between 5 mg and 500 mg, between 5 mg and 400 mg, between 5 mg and 300 mg, between 5 mg and 250 mg, between 5 mg and 100 mg, between 5 mg and 50 mg, between 25 mg and 5000 mg, between 50 mg and 5000 mg, between 100 mg and 5000 mg, between 250 mg and 5000 mg, between 350 mg and 5000 mg, between 500 mg and 5000 mg, between 625 mg and 5000 mg, between 700 mg and 5000 mg, between 900 mg and 5000 mg, between 1000 mg and 5000 mg, between 1500 mg and 5000 mg, between 2000 mg and 5000 mg, between 3500 mg and 5000 mg, between 5 mg and 1000 mg, between 25 mg and 500 mg, between 50 mg and 400 mg, between 100 mg and 300 mg, and between 150 mg and 250 mg) of a ginger component. A composition can be formulated to contain an amount of a ginger component such that a daily dose of between 50 mg to 1000 mg ginger component (e.g., between 50 mg and 900 mg between 50 mg and 850 mg, between 50 mg and 750 mg, between 100 mg and 1000 mg, between 200 mg and 1000 mg, between 350 mg and 1000 mg, between 450 mg and 1000 mg, between 600 mg and 1000 mg, between 700 mg and 1000 mg, between 300 mg to 900 mg, and between 600 mg and 800 mg ginger component) can be conveniently administered. For example, a composition can be formulated to contain 180 mg of a ginger component. When ginger root extract is used, the composition can be formulated to contain an amount of ginger root extract such that a daily dose of between 50 mg to 1000 mg ginger root extract (e.g., between 50 mg and 900 mg between 50 mg and 850 mg, between 50 mg and 750 mg, between 100 mg and 1000 mg, between 200 mg and 1000 mg, between 350 mg and 1000 mg, between 450 mg and 1000 mg, between 600 mg and 1000 mg, between 700 mg and 1000 mg, between 300 mg to 900 mg, and between 600 mg and 800 mg ginger root extract) can be conveniently administered.

Anthocyanin

A composition described herein can contain an anthocyanin. Examples of anthocyanins include, without limitation, aurantinidin, cyaniding, delphinidin, europinidin, luteolinidin, pelargonidin, malvidin, peonidin, petunidin, rosinidin.

Anthocyanins can be synthesized or derivatized from natural sources. In some cases, an anthocyanin can be a component of a plant extract. For example, an anthocyanin can be a component of an extract of an *Aronia*. In some cases, the *Aronia* is *Aronia melanocarpa*. An extract of *Aronia* can be made using an ethanol or hydroalcoholic extraction. In some cases, anthocyanins and plant extracts containing anthocyanins (e.g., *Aronia melanocarpa*) can be obtained commercially. For example, *Aronia melanocarpa* extract can be obtained from Kaden Biochemicals GmbH (Germany).

A composition described herein can contain one or more than one anthocyanin. In some cases, a composition can contain any amount of an anthocyanin. For example, at least 5 percent (e.g., at least 10, 15, 20, 25, 30, 35, 40, 50, 60, 70, 80, or 90 percent) of a dietary supplement can be an anthocyanin. Typically, a dietary supplement contains between 5 mg and 500 mg (e.g., between 5 mg and 450 mg, between 5 mg and 400 mg, between 5 mg and 350 mg, between 5 mg and 320 mg, between 5 mg and 300 mg, between 5 mg and 250 mg, between 5 mg and 150 mg, between 5 mg and 100 mg, between 5 mg and 500 mg, between 10 mg and 500 mg, between 25 mg and 500 mg, between 35 mg and 500 mg, between 50 mg and 500 mg, between 62.5 mg and 500 mg, between 70 mg and 500 mg, between 5 mg and 100 mg, between 25 mg and 500 mg, between 50 mg and 400 mg, and between 100 mg and 300 mg) of an anthocyanin. A composition can be formulated to contain an amount of an such that a daily dose of between 100 mg and 1000 mg (e.g., between 100 and 900 mg, between 100 mg and 800 mg, between 100 mg and 600 mg, between 100 mg and 500 mg, between 100 mg and 400 mg, between 150 mg and 1000 mg, between 250 mg and 1000 mg, between 300 mg and 1000 mg, between 350 mg and 1000 mg, 200 mg and 900 mg, between 250 mg and 800 mg, between 300 mg and 600 mg, and between 350 mg and 500 mg) of the anthocyanin can be conveniently administered.

In some cases, the anthocyanin can be a component of a plant extract. For example, the anthocyanin can be a component of a *Aronia* extract (e.g., *Aronia melanocarpa*). In some cases, the *Aronia* extract is obtained using standard extraction techniques. In some cases, a composition can contain any amount of a plant extract, such as a standard *Aronia melanocarpa* extract. For example, at least 5 percent (e.g., at least 10, 15, 20, 25, 30, 35, 40, 50, 60, 70, 80, or 90 percent) of a dietary supplement can be the plant extract. Typically, a dietary supplement contains between 5 mg and 500 mg (e.g., between 5 mg and 450 mg, between 5 mg and 400 mg, between 5 mg and 350 mg, between 5 mg and 320 mg, between 5 mg and 300 mg, between 5 mg and 250 mg, between 5 mg and 150 mg, between 5 mg and 100 mg, between 5 mg and 500 mg, between 10 mg and 500 mg, between 25 mg and 500 mg, between 35 mg and 500 mg, between 50 mg and 500 mg, between 62.5 mg and 500 mg, between 70 mg and 500 mg, between 5 mg and 100 mg, between 25 mg and 500 mg, between 50 mg and 400 mg, and between 100 mg and 300 mg) of the plant extract. A composition can be formulated to contain an amount of the plant extract such that a daily dose of between 100 mg and 1000 mg (e.g., between 100 and 900 mg, between 100 mg and 800 mg, between 100 mg and 600 mg, between 100 mg and 500 mg, between 100 mg and 400 mg, between 150 mg and 1000 mg, between 250 mg and 1000 mg, between 300 mg and 1000 mg, between 350 mg and 1000 mg, 200 mg and 900 mg, between 250 mg and 800 mg, between 300 mg and 600 mg, and between 350 mg and 500 mg) of the plant extract can be conveniently administered.

Coumarin

A composition described herein can contain a coumarin. Examples of coumarins include, without limitation, decursin, decursinol, nodakenetin, umbelliferon, nodakenin, and β-sitosterol. In some cases, the courmarin is decursinol:

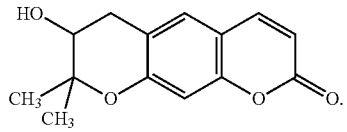 [SMILES: CC1(C)Oc2cc3oc(=O)ccc3cc2CC1O]

Coumarins can be synthesized or derivatized from natural sources. In some cases, a coumarin can be a component of a plant extract. For example, a coumarin can be a component of an extract of *Angelica gigas*. In some cases, the extract of *Angelica gigas* is a root extract. An extract of *Angelica gigas* can be made using an ethanol or hydroalcoholic extraction. In some cases, coumarins and plant extracts containing coumarins (e.g., *Angelica gigas*) can be obtained commercially. For example, *Angelica gigas* root extract can be obtained from FCC Inc., (NJ, USA).

A composition described herein can contain one or more than one coumarin. In some cases, a composition can contain any amount of a coumarin. For example, at least 5 percent (e.g., at least 10, 15, 20, 25, 30, 35, 40, 50, 60, 70, 80, or 90 percent) of a dietary supplement can be an anthocyanin. Typically, a dietary supplement contains between 5 mg and 500 mg (e.g., between 5 mg and 450 mg, between 5 mg and 400 mg, between 5 mg and 350 mg, between 5 mg and 300 mg, between 5 mg and 250 mg, between 5 mg and 150 mg, between 5 mg and 100 mg, between 5 mg and 75 mg, between 10 mg and 500 mg, between 25 mg and 500 mg, between 35 mg and 500 mg, between 50 mg and 500 mg, between 10 mg and 400 mg, between 25 mg and 300 mg, and between 30 mg and 100 mg) of a coumarin. A composition can be formulated to contain an amount of an such that a daily dose of between 50 mg and 1000 mg (e.g., between 50 and 900 mg, between 50 mg and 800 mg, between 50 mg and 600 mg, between 50 mg and 500 mg, between 50 mg and 400 mg, between 50 mg and 300 mg, between 100 mg and 1000 mg, between 150 mg and 1000 mg, between 200 mg and 1000 mg, 75 mg and 900 mg, between 100 mg and 800 mg, between 125 mg and 600 mg, and between 150 mg and 300 mg) of the coumarin can be conveniently administered.

In some cases, the coumarin can be a component of a plant extract. For example, the coumarin can be a component of an *Angelica gigas* extract (e.g., a root extract of *Angelica gigas*). In some cases, the *Angelica gigas* extract is obtained using standard extraction techniques. In some cases, a composition can contain any amount of a plant extract, such as a standard *Angelica gigas* root extract. For example, at least 5 percent (e.g., at least 10, 15, 20, 25, 30, 35, 40, 50, 60, 70, 80, or 90 percent) of a dietary supplement can be the plant extract. Typically, a dietary supplement contains between 5 mg and 500 mg (e.g., between 5 mg and 450 mg, between 5 mg and 400 mg, between 5 mg and 350 mg, between 5 mg and 300 mg, between 5 mg and 250 mg, between 5 mg and 150 mg, between 5 mg and 100 mg, between 5 mg and 75 mg, between 10 mg and 500 mg, between 25 mg and 500 mg, between 35 mg and 500 mg, between 50 mg and 500 mg, between 10 mg and 400 mg, between 25 mg and 300 mg, and between 30 mg and 100 mg) of the plant extract. A composition can be formulated to contain an amount of the plant extract such that a daily dose of between 50 mg and 1000 mg (e.g., between 50 and 900 mg, between 50 mg and 800 mg, between 50 mg and 600 mg, between 50 mg and 500 mg, between 50 mg and 400 mg, between 50 mg and 300 mg, between 100 mg and 1000 mg, between 150 mg and 1000 mg, between 200 mg and 1000 mg, 75 mg and 900 mg, between 100 mg and 800 mg, between 125 mg and 600 mg, and between 150 mg and 300 mg) of the plant extract can be conveniently administered.

Curcuminoid

A composition described herein can contain a curcuminoid. An example of a curcuminoid is curcumin:

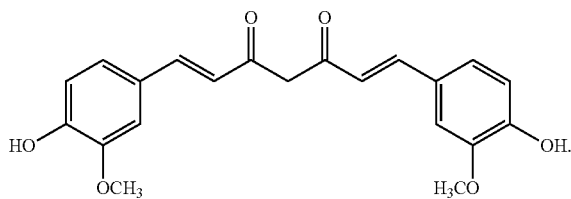 [SMILES: COc1cc(/C=C/C(=O)CC(=O)/C=C/c2ccc(O)c(OC)c2)ccc1O]

Curcuminoids can be synthesized or derivatized from natural sources. In some cases, a curcuminoid can be a component of a plant extract. For example, a curcuminoid can be a component of an extract of turmeric. An extract of turmeric can be made using an ethanol or hydroalcoholic extraction. In some cases, curcuminoid and plant extracts containing curcuminoid (e.g., turmeric) can be obtained commercially. For example, turmeric extract or curcumin can be obtained from BattleChem Inc., (CA, USA).

A composition described herein can contain one or more than one curcuminoid. In some cases, a composition can contain any amount of a curcuminoid. For example, at least 5 percent (e.g., at least 10, 15, 20, 25, 30, 35, 40, 50, 60, 70, 80, or 90 percent) of a dietary supplement can be a curcuminoid. Typically, a dietary supplement contains between 1 mg and 300 mg (e.g., between 1 mg and 250 mg, between 1 mg and 200 mg, between 1 mg and 150 mg, between 1 mg and 100 mg, between 1 mg and 50 mg, between 5 mg and 300 mg, between 10 mg and 300 mg, between 20 mg and 300 mg, between 10 mg and 100 mg, and between 20 mg and 60 mg) of a curcuminoid. A composition can be formulated to contain an amount of a curcuminoid such that a daily dose of between 25 mg and 500 mg (e.g., between 25 mg and 450 mg, between 25 mg and 400 mg, between 25 mg and 350 mg, between 25 mg and 300 mg, between 25 mg and 250 mg, between 10 mg and 500 mg, between 50 mg and 500 mg, between 75 mg and 500 mg, between 90 mg and 500 mg, between 10 mg and 400 mg, between 25 mg and 300 mg, and between 50 mg and 150 mg) of the curcuminoid.

In some cases, the curcuminoid can be a component of a plant extract. For example, the curcuminoid can be a component of a turmeric extract. In some cases, the turmeric extract is obtained using standard extraction techniques. In some cases, a composition can contain any amount of a plant extract, such as a standard turmeric extract. For example, at least 5 percent (e.g., at least 10, 15, 20, 25, 30, 35, 40, 50, 60, 70, 80, or 90 percent) of a dietary supplement can be the plant extract. Typically, a dietary supplement contains between 1 mg and 300 mg (e.g., between 1 mg and 250 mg, between 1 mg and 200 mg, between 1 mg and 150 mg, between 1 mg and 100 mg, between 1 mg and 50 mg, between 5 mg and 300 mg, between 10 mg and 300 mg, between 20 mg and 300 mg, between 10 mg and 100 mg, and between 20 mg and 60 mg) of the plant extract. A composition can be formulated to contain an amount of the plant extract such that a daily dose of between 25 mg and 500 mg (e.g., between 25 mg and 450 mg, between 25 mg and 400 mg, between 25 mg and 350 mg, between 25 mg and 300 mg, between 25 mg and 250 mg, between 10 mg and 500 mg, between 50 mg and 500 mg, between 75 mg and 500 mg, between 90 mg and 500 mg, between 10 mg and 400 mg, between 25 mg and 300 mg, and between 50 mg and 150 mg) of the plant extract can be conveniently administered.

Green Tea

A composition described herein can contain a green tea extract. A green tea extract is an extract derived from *Camellia sinensis*. Any method can be used to obtain a green tea extract. For example, a green tea extract can be obtained by drying (e.g., freeze drying or spray drying) a liquor from an alcoholic, hydroalcoholic, or other hydrocarbon extraction. In some cases, a green tea extract can be dried and standardized to contain at least about 25 percent total phenols. A green tea extract can contain catechin, epicatechin, gallocatechin, epigallocatechin, epicatechin gallate, epicatchingallate, and epigallocatechin gallate. Typically, a composition provided herein contains a green tea extract having at least about 15 percent of catechin group compounds. A green tea extract can be caffeinated or decaffeinated. In some cases, a green tea extract can be obtained commercially. For example, a green tea extract can be obtained from Buckton Scott Nutrition, Inc. (Fairfield, N.J.), Pure World, Inc. (Hackensack, N.J.), Sabinsa Corporation (Piscatawayt, N.J.), or Stauber Performance Ingredients Inc., (Fullerton, Calif.).

A composition provided herein can contain one or more than one green tea extract. In some cases, a composition can contain any amount of a green tea extract. For example, at least 5 percent (e.g., at least 10, 15, 20, 25, 30, 35, 40, 50, 60, 70, 80, or 90 percent) of a dietary supplement can be a green tea extract. Typically, a dietary supplement contains between 5 mg and 500 mg (e.g., between 5 mg and 450 mg, between 5 mg and 400 mg, between 5 mg and 350 mg, between 5 mg and 300 mg, between 5 mg and 250 mg, between 5 mg and 150 mg, between 5 mg and 100 mg, between 5 mg and 75 mg, between 10 mg and 500 mg, between 25 mg and 500 mg, between 35 mg and 500 mg, between 50 mg and 500 mg, between 10 mg and 400 mg, between 25 mg and 300 mg, and between 30 mg and 100 mg) of a green tea extract. A composition can be formulated to contain an amount of a green tea extract such that a daily dose of between 50 mg and 1000 mg (e.g., between 50 and 900 mg, between 50 mg and 800 mg, between 50 mg and 600 mg, between 50 mg and 500 mg, between 50 mg and 400 mg, between 50 mg and 300 mg, between 100 mg and 1000 mg, between 150 mg and 1000 mg, between 200 mg and 1000 mg, 75 mg and 900 mg, between 100 mg and 800 mg, between 125 mg and 600 mg, and between 150 mg and 300 mg) of a green tea extract can be conveniently administered. For example, a composition can be formulated to contain 60 mg of a green tea extract.

Formulations of a Dietary Supplement

Provided herein are compositions (e.g., dietary supplements) containing a combination of an iridoid, a ginger component, an anthocyanin, a coumarin, a curcuminoid, and a green tea extract. In some cases, the composition contains a combination of a Devil's Claw extract, a ginger component, an *Aronia* extract, an *Angelica gigas* extract, a turmeric extract, and a green tea extract. Such compositions can be used to relieve pain, inflammation, and discomfort due to, for example, OA. In some cases, the document provides methods for relieving or reducing pain, inflammation, and/or discomfort due to, for example, OA. Such methods involve administering a composition provided herein.

The compositions provided herein are intended to be ingested (e.g., orally or intragastrically), but can be administered to a mammal by other routes. For example, a composition provided herein can be administered nasally, intravenously, intramuscularly, subcutaneously, sublingually, intrathecally, or intradermally. The route of administration can depend on a variety of factors, such as the environment (e.g., the circumstances resulting in the condition or symptoms) and therapeutic goals.

When administered orally, the composition can be in the form of a tablet or powder. Tablets and powders can be configured to have a unit dosage equal to the daily desired dosage. For example, if a mammal desires 1000 mg of a particular composition, each tablet can be 1000 mg in weight. As used herein, mammals generally refer to humans, but also can include domesticated mammals (e.g., dogs, cats, and livestock such as cows, horses, pigs, or sheep) in which reducing pain, inflammation, and/or stiffness is desirable.

The dosages of a particular composition will depend on many factors including the mode of administration. A dietary supplement of the invention can be formulated in a dose such that an individual receives about 200 mg of Devil's Claw extract, about 180 mg of ginger root extract, about 90 mg Aronia extract, about 50 mg Angelica gigas root extract, about 25 mg curcumin (e.g., turmeric extract), and about 60 mg green tea extract blend in a single tablet.

By way of example, a composition provided herein can be in the form of a liquid, solution, suspension, tablet, powder, cream, mist, atomized vapor, aerosol, soft gelatin capsules, or hard gelatin capsules. Commercial dietary supplements are generally formulated for oral administration. For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. Liquid preparations also can contain pharmaceutically acceptable additives such as suspending agents, emulsifying agents, non-aqueous vehicles, preservatives, buffer salts, flavoring agents, coloring agents, and sweetening agents as appropriate. Preparations for oral administration can be suitably formulated to give controlled release of the compound. Typically, the compositions provided herein are in a powder or tablet form with a fast disintegration time.

A composition provided herein can contain a pharmaceutically acceptable carrier for in vivo administration to a mammal. Such pharmaceutically acceptable carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include water, alcohol, saline, and buffered solutions. Pharmaceutically acceptable carriers also can include physiologically acceptable aqueous vehicles (e.g., physiological saline) or other known carriers appropriate to specific routes of administration. Preservatives, flavorings, and other additives such as, for example, proteins, anti-microbials, chelating agents, inert gases, and the like also can be present in a composition.

The invention will be further described in the following examples, which do not limit the scope of the invention described in the claims.

EXAMPLES

Example 1—Dietary Supplement Formulation

Tablets were prepared using amounts of each plant extract shown in Table 1.

TABLE 1

| Plant Extract | Amount (mg per serving) |
| --- | --- |
| Devil's Claw | 200 |
| Ginger root | 180 |
| Aronia (Chokeberry) | 90 |
| Angelica gigas root (Decursinol) | 50 |
| Curcumin (Turmeric) | 25 |
| Green Tea | 60 |

Example 2—Anti-Inflammatory Blend Formulation

The following study was randomized, single-blind, and placebo-controlled. 24 volunteers claiming to have some level of joint and muscle discomfort were recruited for the study. The age spread of volunteers was 26-63 and included 15 women and 9 men. All volunteers were randomly assigned to 1 of 2 groups: either the placebo or treatment. A serum sample was collected from each participant on "day 0" and an initial questionnaire was completed. Participants were then given 2 weeks worth of product (the formulation in Example 1) or placebo and instructed to take 4 tablets per day and fill out a questionnaire at "day 7" and "day 14" of the study. A second serum sample was collected from each participant on "day 14", the final day of the study. Compliance checks were conducted after one and two weeks.

CRP Analysis:

Serum samples were stored in a −80° C. freezer until the time of assay. High Sensitivity C-Reactive Protein (hs-CRP) assays were performed using immunoturbidimetric assay kit reagents from Kamiya Biomedical Company, product # KAI060. Measurements were performed on a plate reader Spectromax M2 (Molecular Devices, CA).

Statistical Analysis:

The goals of the analysis were to compare control and treatment group scores over the course of the study and to calculate the temporal dynamics of well-being indices for both groups. The analysis was based on the two-sample Kolmogorov-Smirnov statistical test. This test allows one to accept or reject the null hypothesis that two samples of equal or distinct size are drawn from the same distribution (i.e. the treatment does not have any significant effect). The computed value of the test statistic lead to a significance level (P-value) with which the null hypothesis is rejected.

$$S = \sqrt{\frac{mn}{m+n}} \max_x |F_m(x) - F_n(x)|$$

where m and n are sample sizes and $F_n(x)$ is the value of the empirical distribution function at point x for the sample of size n.

According to Kolmogorov-Smirnov theorem, the asymptotic distribution of the statistic S is independent of the assumed underlying distribution in the null hypothesis and has the following distribution function:

$$K(t) = 1 - 2\sum_{k=1}^{\infty} (-1)^{k-1} e^{-2k^2 t^2}$$

This formula was used for computing the P-values.

Twenty-three participants completed the study. One participant from the treatment group dropped out after one week. None of the volunteers reported any adverse affects from taking the supplements.

The non-specific inflammation marker—C-reactive protein (CRP) was measured in serum samples taken at the beginning and end of the study. Only 8 participants had slightly elevated (measurable) levels. No meaningful trend either way was found.

The Western Ontario and McMaster Universities index (WOMAC) was used for the assessment. This index includes 24 questions divided into three categories: pain, stiffness, and physical function. Participants were required to evaluate each question on a 5-score scale (0-4) before and after treatment. The objective of the evaluation is to ascertain the effect of the product on the participants' well-being as measured by the total WOMAC score and the average scores in each category. Individual scores of participants were normalized by dividing the total score within each category (pain, stiffness, and physical function) by the number of questions in the category. The normalized WOMAC score was calculated the same way. Normalized scores are shown in Table 2.

while P-values close to 1 indicate that the difference is very significant. P-values for the two sample comparison (placebo vs. treatment) are given in Table 3.

TABLE 3

P-values for the two sample comparison (placebo vs. treatment) by week and category.

|  | Week 0 | Week 1 | Week 2 |
|---|---|---|---|
| WOMAC | 0.153 | 0.900 | 0.951 |
| Pain | 0.153 | 0.752 | 0.986 |
| Stiffness | 0.482 | 0.966 | 0.841 |
| Physical Function | 0.482 | 0.900 | 0.946 |

As shown in Table 3, the difference in WOMAC score is insignificant initially, progresses greatly after one week of treatment, and reaches almost an absolute maximum by the end of week 2. A similar trend was observed for subcategories.

The temporal dynamics of P-values during the course of the study is presented in Table 4.

TABLE 2

|  |  | Pain | | | Stiffness | | | Physical Function | | | WOMAC | | |
|---|---|---|---|---|---|---|---|---|---|---|---|---|---|
| Week |  | 0 | 1 | 2 | 0 | 1 | 2 | 0 | 1 | 2 | 0 | 1 | 2 |
| Placebo | CH | 0.8 | 1.4 | 1.0 | 1.5 | 2.0 | 2.0 | 0.5 | 1.1 | 0.8 | 0.7 | 1.3 | 1.0 |
|  | MW | 0.0 | 0.2 | 0.2 | 1.5 | 1.5 | 0.5 | 0.5 | 0.3 | 0.2 | 0.5 | 0.3 | 0.2 |
|  | TI | 0.0 | 0.0 | 1.4 | 1.5 | 1.0 | 1.0 | 0.4 | 0.2 | 1.3 | 0.4 | 0.2 | 1.3 |
|  | AR | 1.2 | 0.8 | 1.2 | 2.0 | 2.0 | 2.5 | 0.9 | 0.7 | 0.7 | 1.0 | 0.8 | 1.0 |
|  | WS | 0.8 | 1.4 | 1.6 | 2.0 | 2.0 | 2.0 | 1.1 | 1.3 | 1.4 | 1.1 | 1.4 | 1.5 |
|  | JP | 2.2 | 2.0 | 1.6 | 4.0 | 2.0 | 2.0 | 2.4 | 2.6 | 1.4 | 2.5 | 2.4 | 1.5 |
|  | JG | 2.0 | 2.4 | 2.6 | 3.5 | 3.0 | 3.5 | 2.4 | 2.3 | 2.2 | 2.4 | 2.3 | 2.4 |
|  | JS | 1.0 | 1.0 | 0.6 | 2.5 | 2.0 | 1.0 | 1.8 | 1.8 | 0.8 | 1.7 | 1.6 | 0.8 |
|  | CS | 1.2 | 1.2 | 1.2 | 1.5 | 1.5 | 1.0 | 1.2 | 1.2 | 1.2 | 1.2 | 1.2 | 1.2 |
|  | EA | 0.0 | 0.0 | 0.0 | 0.5 | 0.0 | 0.5 | 0.3 | 0.1 | 0.0 | 0.2 | 0.0 | 0.0 |
|  | DCW | 2.4 | 2.0 | 1.6 | 2.5 | 2.5 | 1.5 | 2.1 | 2.1 | 1.4 | 2.2 | 2.1 | 1.5 |
|  | TS | 2.2 | 2.2 | 1.4 | 1.0 | 1.0 | 1.0 | 2.3 | 2.3 | 1.3 | 2.1 | 2.1 | 1.3 |
| Aver |  | 1.2 | 1.2 | 1.2 | 2.0 | 1.7 | 1.5 | 1.3 | 1.3 | 1.1 | 1.3 | 1.3 | 1.1 |
| Treatment | DS | 0.2 | 0.2 | 0.0 | 1.0 | 0.5 | 0.5 | 0.1 | 0.1 | 0.0 | 0.2 | 0.2 | 0.0 |
|  | CC | 2.4 | 2.6 | 2.6 | 3.0 | 2.5 | 2.5 | 2.3 | 2.4 | 2.1 | 2.3 | 2.4 | 2.3 |
|  | SF | 0.8 | 1.0 | 0.4 | 2.5 | 2.0 | 1.5 | 1.1 | 1.0 | 1.0 | 1.2 | 1.1 | 0.9 |
|  | JK | 0.2 | 0.2 | 0.2 | 0.5 | 0.5 | 0.5 | 0.3 | 0.0 | 0.1 | 0.3 | 0.1 | 0.1 |
|  | DL | 0.2 | 0.0 | 0.2 | 0.5 | 0.5 | 0.5 | 0.3 | 0.1 | 0.0 | 0.3 | 0.1 | 0.1 |
|  | TC | 1.6 | 0.6 | 0.0 | 1.0 | 0.5 | 0.5 | 1.4 | 0.7 | 0.4 | 1.4 | 0.7 | 0.3 |
|  | BM | 1.4 | 1.4 | 0.8 | 2.0 | 1.0 | 1.0 | 2.1 | 1.4 | 1.1 | 1.9 | 1.3 | 1.0 |
|  | DCP | 0.6 | 0.6 | 0.2 | 0.5 | 1.0 | 0.0 | 0.3 | 0.6 | 0.1 | 0.4 | 0.6 | 0.1 |
|  | DC | 1.0 | 0.6 | 0.2 | 2.0 | 0.5 | 0.0 | 0.8 | 0.3 | 0.1 | 1.0 | 0.4 | 0.1 |
|  | EM | 1.2 | 1.2 | 0.2 | 2.5 | 0.5 | 1.0 | 0.8 | 0.4 | 0.1 | 1.0 | 0.6 | 0.2 |
|  | CHA | 0.4 | 0.2 | 0.4 | 1.0 | 0.0 | 0.0 | 0.5 | 0.1 | 0.3 | 0.5 | 0.1 | 0.3 |
|  | SFO | 0.6 | 0.6 |  | 2.0 | 0.5 |  | 0.8 | 0.1 |  | 0.9 | 0.3 |  |
| Aver |  | 0.9 | 0.8 | 0.5 | 1.5 | 0.8 | 0.7 | 0.9 | 0.6 | 0.5 | 0.9 | 0.7 | 0.5 |

Samples were defined as sets of normalized individual scores for participants in placebo and treatment groups for each category and for WOMAC for weeks 0, 1, and 2.

The results of the analysis are shown graphically in FIG. 1. As can be seen from FIG. 1, the average value of pain, stiffness, and physical function indicators, along with the normalized WOMAC score, decreased dramatically in treatment group, while varying insignificantly in the placebo group.

Figure 2:
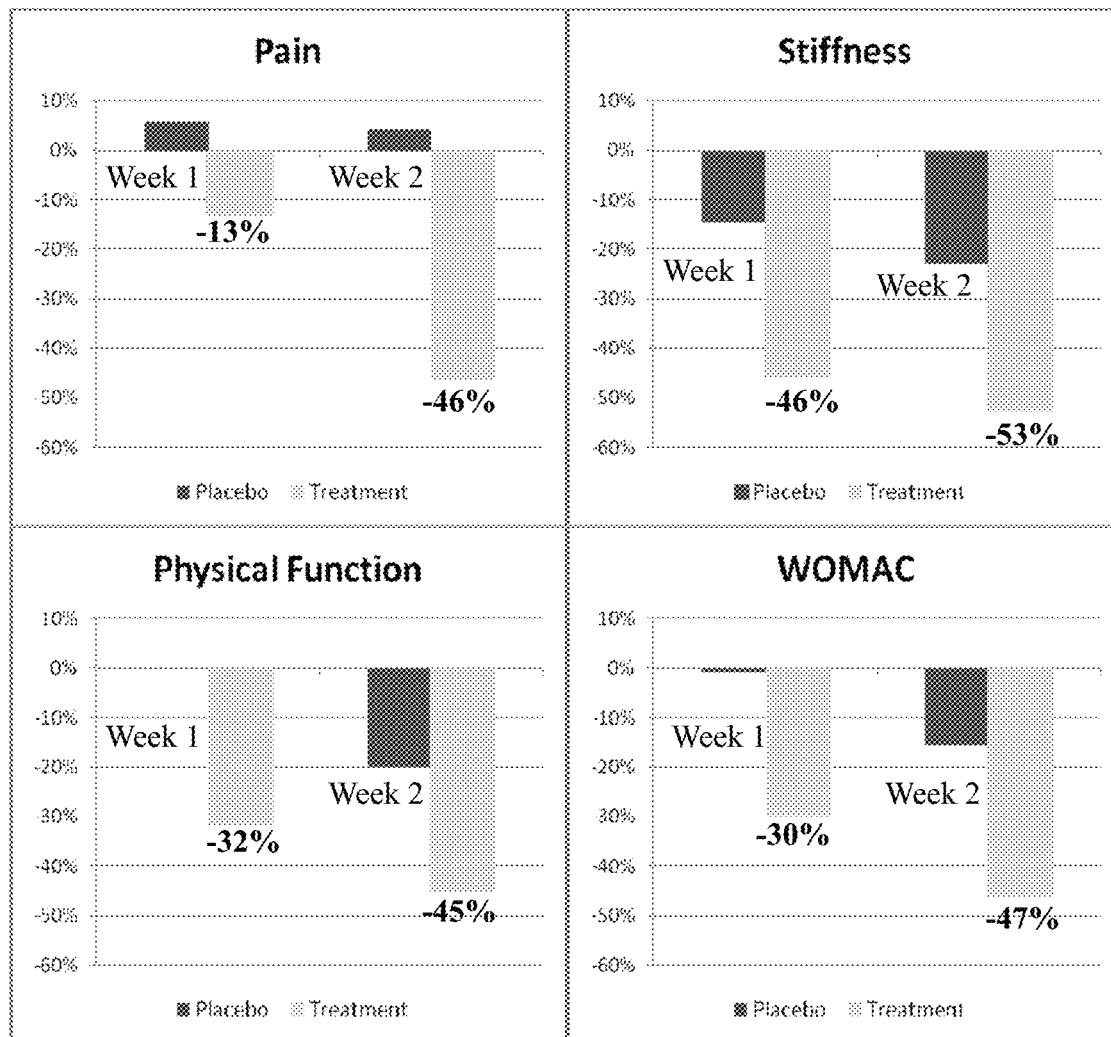
FIG. 2 is a bar graph of the net changes of the normalized WOMAC scores by week for each category tested.

The net changes of the normalized scores by category compared to their initial values are shown in FIG. 2.

The statistical significance of the difference between placebo and treatment groups is characterized by P-value. Small P-value means that the difference is insignificant,

TABLE 4

Temporal Dynamics of P-value by group and category.

|  |  | Week 1 vs Week 0 | Week 2 vs Week 0 | Week 2 vs Week 1 |
|---|---|---|---|---|
| Placebo | WOMAC | 0.004 | 0.482 | 0.153 |
|  | Pain | 0.004 | 0.153 | 0.153 |
|  | Stiffness | 0.004 | 0.153 | 0.153 |
|  | Physical Function | 0.004 | 0.482 | 0.482 |
| Treatment | WOMAC | 0.482 | 0.854 | 0.363 |
|  | Pain | 0.004 | 0.865 | 0.865 |
|  | Stiffness | 0.752 | 0.708 | 0.014 |

TABLE 4-continued

Temporal Dynamics of P-value by group and category.

|  | Week 1 vs Week 0 | Week 2 vs Week 0 | Week 2 vs Week 1 |
|---|---|---|---|
| Physical Function | 0.482 | 0.828 | 0.0002 |

Analysis of week by week dynamics of the normalized scores reveals no significant change in placebo group. Some variation of P-value is due to the small sample size. Results for the treatment group show that significant improvement of participants' conditions occurs already by the end of week 1 and further improves during week 2.

The conducted placebo-controlled, 2-week supplementation clinical study on 24 human volunteers with symptoms of joint and physical discomfort indicated treatment with the formulation of Example 1 significantly improved the participants' well-being. Physical conditions improved by 30% after one week, and reached 47% after two weeks of supplementation. No significant change was observed in the placebo group. None of the volunteers reported any adverse affects from taking the supplements.

A follow-on study was conducted, similar to that described above, using the supplement of Example 1 on nearly 100 volunteers. In this study, both treatment and placebo groups were told before receiving the treatment or placebo of the study's intended purpose and potential results. Both treatment and placebo groups showed approximately 20% improvement in all physical parameters. No statistical significance between the treatment and placebo groups was observed.

Example 3—Dietary Supplement Formulation Reduces TNF-α Activated Inflammation

A randomized, single-blind, and placebo-controlled study was performed. Eleven volunteers were recruited for the study. All volunteers were randomly assigned to 1 of 2 groups: either the placebo or treatment (seven in the treatment group and four in the placebo group).

General Methods

Reagents:
Krebs-HEPES buffer, Noxygen, 20 mM, pH: 7.4, Model: NOX-7.6.1-500 mL
Tumor Necrosis Factor—Alpha (TNF-α), Sigma, Cat No. T6674
1-Hydroxy-4-phosphono-oxy-2,2,6,6-tetramethyl-piperidine (PPH), Noxygen, Model: NOX-4.2-50 mg, MW: 253.2
Deferoxamine methanesulfonate (DF), Noxygen, Model: NOX-9.1-100 mg, MW: 656.79
Diethyldithiocarbamic acid sodium salt (DETC), Noxygen, Model: NOX-10.1-1 g, MW: 225.31
Heparin, Sigma, Cat No. H3393
Whole human blood Equipment:
Bruker BenchTop EPR spectrometer E-Scan equipped with Temperature & Gas Controller NOX-E.3-TGC Stock Solutions Preparation:

Stock solutions for use in the method described below were prepared as follows. A stock solution of PPH with a concentration of 10818.6 µM was prepared by dissolving 8.3 mg of PPH in 3.03 mL of Krebs-HEPES buffer. 100 µL aliquots were prepared and frozen at −80° C. for later use. A stock solution of DF with a concentration of 1137 µM was prepared by dissolving 8.4 mg of DF in 11.25 mL of Krebs-HEPES buffer. The solution was separated into 40 µL aliquots and frozen at −80° C. for later use. A stock solution of DETC with a concentration of 222 µM was prepared by dissolving 20 mg of DETC in 10 mL of Krebs-HEPES buffer. This solution was separated into 40 µL aliquots and frozen at −80° C. Preparation of a stock solution of TNF-α in Krebs-HEPES buffer with a concentration of 1000 ng/mL involved dissolving 10 µg of TNF-α in 10 mL of buffer. 125 µL aliquots were prepared and frozen at −80° C. for later use. A 1000 U/mL stock solution of Heparin in Krebs-HEPES buffer was prepared by dissolving 51.4 mg of Heparin in 9.25 mL of buffer.

Working Solutions

The PPH solution was prepared by thawing the stock reagents and vortexing. 763 µL of Krebs-HEPES buffer, 100 µL of Heparin (for 100 U/mL), 92.4 µL of PPH (for 1000 µM), 22.5 µL of DETC (5 µM), and 22.0 µL of DF (25 µM) were then combined. The mixture was then placed into an ice bath until needed. The solution of TNF-α was thawed and vortexed. The stock was then diluted as appropriate with Krebs-HEPES buffer to obtain concentrations of 160 and 240 ng/mL. The solutions were then placed in an ice bath.

Procedure

The EPR and Temperature/Gas regulator were prepared for use. The temperature regulator was set to 37.0° C., the pressure set to 25 mmHg, and the oxygen concentration set to 7.4%. The instrument setting was as follows: Center field: 3472.578 G Sweep width: 60,000 G, Static field: 3458.578 G, Frequency: 9.76 GHz, Attenuator: 3.0 dB, Power: 23.05 mW, Gain: $1.00 \times 10^3$, Modulation frequency: 86.00 kHz, Modulation Amplitude: 2.19 G, Modulation Phase: 358.61 deg, Time constant: 40.96 msec, Conversion time: 110.24 msec, Sweep time: 5.24 sec. Number of scans: 10, number of points: 46, experimental time: 58 minutes.

As a zero point, 4 mL of blood was collected in a sodium heparin Vacutainer. The volunteer was then provided three tablets of the formulation of Example 1 or placebo, and instructed to return after 2 hours and to continue fasting until the testing was completed. 20 µL each of Krebs-HEPES buffer, PPH solution, whole blood, and TNF-α solution were combined to a total volume of 80 µL. 45 µL of the working solutions was transferred to a 50 µL capillary tube and sealed with Critoseal. The final concentration of the solutions in the capillary tube were: 250 µM PPH solution (which includes 25 U/mL of heparin) and 40 ng/mL TNF-α. The sealed sample was then inserted into the capillary holder of the EPR instrument. After the EPR measurement was complete, another sample was prepared with the same blood sample but with a final concentration of 60 ng/mL of TNF-α. After two hours, a second whole-blood sample in a sodium heparin Vacutainer was collected from the volunteer and the measurements described above were repeated on the second sample.

Figure 3:
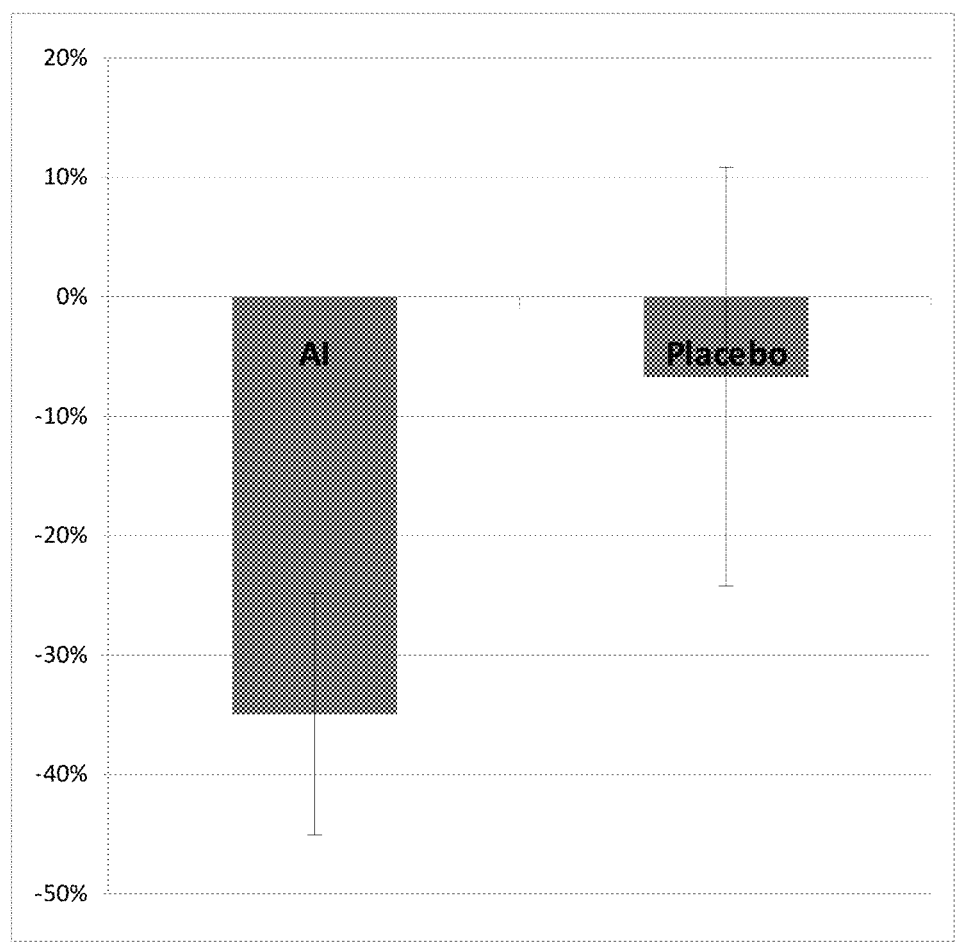
FIG. 3 is a bar graph of the averaged change in EPR amplitude corresponding to ROS production for the test and placebo group.

As shown in FIG. 3, the treatment group decreased by 35%±10% (p=0.030) in ROS production amplitude and the placebo group decreased 7%±18% (p=0.562). These results demonstrate that administration of the dietary supplement of Example 1 can reduce TNF-α induced inflammation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claim.

What is claimed is:

1. A dietary supplement for reducing pain, stiffness, or inflammation in a mammal, the dietary supplement comprising a mixture of:
   (a) about 37 mg to about 63 mg of Devil's Claw extract;
   (b) about 16 mg to about 29 mg of *Aronia* extract;
   (c) about 8 mg to about 16 mg of *Angelica gigas* extract and
   (d) about 1 mg to about 50 mg of a turmeric extract.

2. The dietary supplement of claim 1, wherein said dietary supplement is in the form of a tablet, a powder, or a liquid.

3. The dietary supplement of claim 1, further comprising a ginger component.

4. The dietary supplement of claim 1, further comprising a green tea extract.

5. The dietary supplement of claim 1, comprising:
   (a) about 50 mg of the Devil's Claw extract;
   (b) about 22.5 mg of the *Aronia* extract; and
   (c) about 12.5 mg of the *Angelica gigas* extract.

6. The dietary supplement of claim 1, wherein said dietary supplement is a single tablet.

7. The dietary supplement of claim 1, wherein said dietary supplement includes three or four tablets.

8. A method of reducing pain, stiffness, or inflammation in a mammal, said method comprising administering to said mammal an effective amount of the dietary supplement according to claim 1.

9. The method of claim 8, wherein daily administration of said dietary supplement to said mammal for at least one week reduces pain, stiffness, or inflammation in said mammal.

10. A dietary supplement for reducing pain, stiffness, or inflammation in a mammal, the dietary supplement comprising a mixture of:
    (a) about 5 mg to about 100 mg of a Devil's Claw extract;
    (b) about 5 mg to about 100 mg of an *Aronia* extract;
    (c) about 1 mg to about 50 mg of a turmeric extract; and
    (d) about 5 mg to about 75 mg of a green tea extract.

11. The dietary supplement of claim 10, further comprising about 20 mg to about 60 mg of the turmeric extract.

12. The dietary supplement of claim 10, further comprising a ginger component.

13. The dietary supplement of claim 10, further comprising an *Angelica gigas* extract.

14. The dietary supplement of claim 13, further comprising about 5 mg to about 75 mg of the *Angelica gigas* extract.

15. The dietary supplement of claim 13, further comprising about 35 mg to about 65 mg of the *Angelica gigas* extract.

16. The dietary supplement of claim 10, wherein the dietary supplement comprises about 5 mg to about 50 mg of a ginger component.

17. The dietary supplement of claim 10, wherein said dietary supplement is in the form of a tablet, a powder, or a liquid.

18. The dietary supplement of claim 10, wherein said dietary supplement is a single tablet.

19. A method of reducing pain, stiffness, or inflammation in a mammal, said method comprising administering to said mammal an effective amount of the dietary supplement according to claim 10.

20. The method of claim 19, wherein daily administration of said dietary supplement to said mammal for at least one week reduces pain, stiffness, or inflammation in said mammal.

* * * * *